United States Patent [19]
Wickerhauser

[11] 4,104,266
[45] Aug. 1, 1978

[54] METHOD FOR PREPARATION OF ANTIHEMOPHILIC FACTOR

[75] Inventor: Milan Wickerhauser, Bethesda, Md.

[73] Assignee: American National Red Cross, Washington, D.C.

[21] Appl. No.: 787,425

[22] Filed: Apr. 14, 1977

[51] Int. Cl.² .................... A23J 1/06; A61K 35/14
[52] U.S. Cl. ............................ 260/112 B; 424/101
[58] Field of Search ................. 260/112 B; 424/101

[56] References Cited

U.S. PATENT DOCUMENTS

| | | | |
|---|---|---|---|
| 3,631,018 | 12/1971 | Shanbrom et al. | 260/112 B |
| 3,652,530 | 3/1972 | Johnson et al. | 260/112 B |
| 4,025,618 | 5/1977 | Garber et al. | 424/101 |

OTHER PUBLICATIONS

Hersshgold et al., J. Lab. Clinical Medicine, vol. 67, No. 1, (Jan.) 1966, pp. 23–32.

*Primary Examiner*—Walter C. Danison
*Attorney, Agent, or Firm*—Holman & Stern

[57] ABSTRACT

An improved method for preparation of purified AHF is disclosed. The method includes the cryoprecipitation of plasma, followed by a cold extraction of the cryoprecipitate at low temperature, approximately 0° C, to obtain a cold insoluble fraction. The cold insoluble fraction is then extracted at approximately 21° C to obtain an AHF-containing solution. By incorporating a cold extraction step to selectively remove some impurities prior to extraction of AHF from cryoprecipitate, there has been obtained a substantial increase in the purity as well as the potency of AHF without the use of any new precipitant or adsorbent in the system.

4 Claims, No Drawings

METHOD FOR PREPARATION OF ANTIHEMOPHILIC FACTOR

BACKGROUND AND SUMMARY OF THE INVENTION

Antihemophilic factor (AHF) of intermediate purity as prepared by the method described in U.S. Pat. No. 3,652,530 has been found to contain about 10 factor VIII units per ml at 20-25 fold purification over plasma. The method of preparation described in U.S. Pat. No. 3,652,530 is based on the extraction of the AHF-containing fraction from cryoprecipitate followed by partial purification with aluminum hydroxide. A product which is more concentrated than that obtained by the method of U.S. Pat. No. 3,652,530 is desirable to facilitate administration of AHF by syringe rather than by infusion, particularly for home treatment of hemophiliacs.

Previous attempts to improve factor VIII potency of the AHF-containing concentrate by reducing the volume of the extracting buffer have resulted in deteriorated filtrability of the AHF solution and decreased solubility of the lyophilized AHF product, presumably because of excessive protein content. This suggests that increased purification is needed in order to permit preparation of a more concentrated, readily soluble AHF product. Highly purified and concentrated AHF has been previously prepared by fractionation with polyethylene glycol, but at the expense of significant AHF losses.

The present invention is concerned with an improved method for increasing the purification and concentration of AHF, based on the principle of fractional extraction. By incorporating a cold extraction step to selectively remove some impurities prior to extraction of AHF from cryoprecipitate, there has been obtained a substantial increase in the purity as well as the potency of AHF without adding any new reagent to the system.

The method of the present invention includes the steps of: (a) cryoprecipitation of plasma; (b) a cold extraction of the cryoprecipitate at low temperature, approximately 0° C, to obtain a cold insoluble fraction having cold soluble impurities removed therefrom; and (c) extraction of the cold insoluble fraction at a temperature of approximately 21° C to obtain a solution containing AHF. The solution containing AHF is then subjected to further treatment including deprothrombinization with aluminum hydroxide gel, stabilization with sodium citrate and filtration, after which the AHF-containing concentrate is recovered by means such as freezing and lyophilization.

DESCRIPTION OF THE PREFERRED EMBODIMENTS

The present inventive procedure will be more fully understood by reference to the following Flow Diagram in which there appears a representation of the procedure for preparation of human AHF in accordance with the present invention:

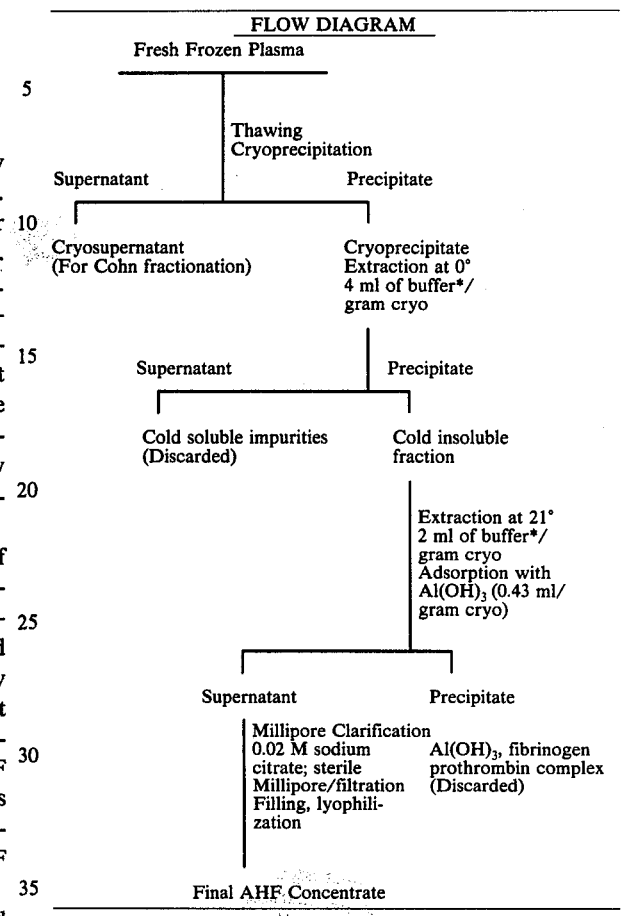

*0.02 M Tris-HCl buffer, pH 7.0

Generally, the present invention includes large scale cryoprecipitation of fresh-frozen human plasma. Such fresh-frozen plasma may be prepared by well known procedures as described, for example, in U.S. Pat. No. 3,652,530 to Johnson et al., which is incorporated herein by reference. Immediately upon removal from storage, the plastic bags with fresh-frozen plasma are placed in wire baskets or other suitable container and rinsed with ice cold (−5° C) 70% ethanol. The fresh-frozen plasma is then allowed to thaw at 4° C, after which the bags are rinsed with distilled water at 5° C to remove residual ethanol.

The plasma is next removed from the bags and subjected to chopping in order to form a slush. The chopped plasma in a thick, homogeneous slush form is then transferred to a jacketed, stainless steel tank for cryoprecipitation. While in the tank, the plasma is allowed to continue to thaw at 4° C to form a liquid at 0° C containing a small amount of ice. During this thawing procedure, water at 5°-7° C is passed through the jacket of the tank, first in intermittent surges, then in continuous flow. At the same time, the plasma is subjected to stirring, first manually, then by mechanical means. The cryoprecipitate which forms may be recovered by centrifugation.

In the cold extraction step, the obtained cryoprecipitate is immersed in a low ionic strength buffer solution containing tris (hydroxymethyl) aminomethane, hereinafter sometimes referred to as TRIS. The operable range of TRIS concentration, in this step as well as in the subsequent extraction step, is from about 0.005 to about 0.04 M, preferably 0.02 M, and with a pH of 7.0. The amount of buffer employed in this cold extraction step is generally about 4 ml Tris buffer per gram of cryoprecipitate being treated. The temperature should be maintained at 0° C. During this time, the buffer solution with cryoprecipitate immersed therein is subjected to chopping and stirring, after which the suspension is allowed to settle and separate. The cryoprecipitate, with cold soluble impurities removed, may be recovered by suitable well known recovery procedures, including centrifugation and filtration.

In the second extraction step, the AHF-containing cryoprecipitate recovered from the cold extraction step is subjected to treatment with the TRIS buffer at a temperature of 21° C. In this step, the pH is adjusted to maintain a value of 7.0 by the addition of 0.1N hydrochloric acid. The amount of buffer employed in this extraction step is generally about 2 ml Tris buffer per gram of cryoprecipitate being treated. The AHF-rich supernatant which is obtained is absorbed with 430 ml of aluminum hydroxide gel per kilogram of original cryoprecipitate, with adjustment of pH to 7.0 by the use of 0.1N hydrochloric acid. The suspension is then centrifuged to remove the aluminum hydroxide. The AHF-rich supernatant from the centrifuge is then filtered and stabilized with sodium citrate in a range of 0.01–0.02M final concentration and the pH is adjusted to approximately 7.0 with 0.1N hydrochloric acid. The AHF-rich solution is then subjected to further filtration and sterilization, after which the final AHF-rich solution is quick-frozen in liquid nitrogen and stored at −70° C for subsequent lyophilization.

A comparison between the method of U.S. Pat. No. 3,652,530 and the present invention is shown in Table I.

Table 1

| Purification Step | Old Method (U.S. Pat. No. 3,652,530) | New Method (present invention) |
|---|---|---|
| Plasma thawing and precipitation | James and Wickerhauser 1972, Vox Sang. 23:402 | Same |
| Cold extraction step | None | 4 ml Tris buffer/gcryo |
| AHF extraction step | 3–3.5 ml Tris buffer per gram cryo | 2 ml Tris buffer/gram cryo |
| Deprothrombinization with Al(OH)$_3$, stabilization with sodium citrate, filtration | James and Wickerhauser 1972, Vox Sang. 23:402. | Same |
| Freezing | At −30° C | In liquid nitrogen |
| Lyophilization | Shelf temperature up to 38° C. (Squibb) | Shelf temperature between 25–38° C |
| Volume ratio before and after lyophilization | 50/25 ml | 25/10 ml |

EXAMPLE I

Fresh-frozen plasma (295.7 l., 1,322 units) was removed from storage at −20° C and placed in 35 × 27 × 24 inch wire baskets. The plastic bags with 200-250 ml of fresh-frozen plasma were immediately rinsed with 70% EtOH at −5° C and thawed for 8.5 hrs. at 4° C. Residual ethanol was rinsed from the plasma bags with DD-H$_2$O at 5° C just prior to chopping. Chopping was accomplished with a Hobart Chopper (Model VCM 40) at room temperature and required about 2½ hrs. The chopped plasma in a thick, homogeneous slush form was transferred to a fully-jacketed, 400 l. Pfaudler tank for cryoprecipitation. The fresh frozen plasma slush was thawed for about 5-6 hrs. at 4° C to a liquid at 0° C containing ⅛ inch of ice. A detailed description of the thawing process is as follows:

| Time | Method |
|---|---|
| 0 – 0.5 hrs. | Approx. 20 intermittent surges, each of 10–20 sec. duration of H$_2$O at 5–7° C were forced through the jacket; the plasma was manually pushed and stirred during this period. |
| 0.5 – 2.5 hrs. | H$_2$O at 5–7° C was run through the tank jacket at a rate of 300–500 l./hr.; the temperature of effluent H$_2$O was 2–3° C; the plasma was manually stirred during this period. |
| 2.5 – 6 hrs. | H$_2$O at 5–7° C was run through the jacket at 700–1000 l/hr.; the temperature of effluent was 3–4° C; the plasma was stirred by a Lightning motor, Model D-3, 1725 RPM, with a ¾ inch bar and two 11-inch propellers; two propellers were used for 45 min., then one was removed to prevent excess foaming. |

The cryoprecipitate was recovered by continuous-flow centrifugation using two Model 16 Sharples centrifuges. During centrifugation, the flow rate was 55.5 l./hr. and the supernatant in an amount of 292 l. was collected at 1.0° C. The cryoprecipitate weighed 2910 gm.

The cryoprecipitate was immersed in 11.64 l. of 0.02 M TRIS buffer, pH 7.00, temp. 0° C, and manually stirred with a spatula for approximately 30 seconds. A fraction of the wash buffer, 6.5 l., was supercooled to form a fine ice which enhanced chopping and maintained the temperature of 0° C throughout the washing step. The cryoprecipitate was chopped into 2–3 mm$^3$ pieces using a Hobart Chopper, Model 8141. The chopped cryoprecipitate was stirred with a Vibromixer, Model E-2, for 19 minutes at low speed and 0° C was maintained. The wash suspension was allowed to settle and separate for 18 minutes. The cryoprecipitate was recovered by decanting as much supernatant as possible and passing it through a single layer of surgical gauze. The remaining suspension containing fine cryoprecipitate particles was separated in the container, a 60 l. two-handled can, using a 4-level stainless steel mesh separator.

Cryoprecipitate was recovered from the wash filtrate (11.7 kg.) by centrifugation using two Sharples centrifuges with no overflow. The supernatant, 10.9 kg., was collected at 1.0° C and it had a pH of 7.38. The cryoprecipitate, 620 gm., was manually chopped into ½ in$^2$ pieces and added to the extraction suspension 9 minutes after initial extraction began.

In the second extraction procedure, the cryoprecipitate was extracted in 5.82 l. of 0.02 M TRIS buffer, pH 7.00, for 23 minutes at 21° C. Mixing was accomplished with a Vibromixer, Model E-2, the first 5 minutes of the mixing being carried out at high speed, and also with 2 minutes at high speed after addition of the wash cryoprecipitate, the remainder being at low speed. The extraction temperature was achieved by placing a 60 l. two-handled can containing the cryoprecipitate in a Pfaudler tank with H$_2$O at 30°–35° C. The buffer was slowly added to the cryoprecipitate and manual stirring was continuous until a temperature of 22° C was achieved. Addition of the wash cryoprecipitate, 620 gm., lowered the temperature of the suspension to 21° C. The pH was adjusted from 7.36 to 7.00 by adding 220 ml of 0.1N hydrochloric acid. Such adjustment was initiated 5 minutes before termination of the extraction step. The extract suspension weighed 9.2 kg.

The TRIS extract was absorbed with 1171 ml of Al(OH)$_3$ gel (Rehsorptar, Control No. P1184). The pH was immediately adjusted from 7.15 to 7.00 with 96 ml of 0.1N hydrochloric acid. The Al(OH)$_3$ suspension, 10.6 kg., was mixed at low speed using the E-2 Vibromixer for 15 minutes.

The Al(OH)$_3$ suspension was centrifuged in two Sharples centrifuges with no overflow for 42 minutes. The supernatant, 8.5 kg., was recovered at 20° C and the Al(OH)$_3$ precipitate weighed 1.64 kg.

The Al(OH)$_3$ supernatant was clarified through a 293 mm Millipore (Millipore Company) filter containing a glass prefilter and 1.2 $\mu$ membrane. Filtration of the supernatant, 8.5 kg., required 4 minutes and 8.16 l. of filtrate was recovered.

The clarified supernatant was stabilized with 340 ml of 0.5 M sodium citrate and the pH was adjusted from 7.34 to 7.05 with 130 ml of 0.1N hydrochloric acid. This solution, 8.630 l., was clarified through a 293 mm Millipore filter containing a glass prefilter and a 0.45 $\mu$ membrane. Filtration took 5 minutes and 8.560 l. of filtrate was recovered.

Sterilization was accomplished by passage through a 293 mm Millipore filter containing a glass prefilter, with 1.2, 0.45 and 0.22 $\mu$ membranes. Filtration required 31 minutes and 8.476 l. of final solution was recovered.

Table II

Quantitation of Yields and Recoveries of AHF Concentrates

| Purification Step | Volume (liters) | Factor VIII Activity Units/ml | Factor VIII Activity Total Units | Recovery Units/liter plasma | Protein mg/ml | Fibrinogen mg/ml | Specific Activity | Purification over Plasma |
|---|---|---|---|---|---|---|---|---|
| Cryro-rich plasma | 295 | .56 | 165,200 | 560 | — | — | 0.009** | 0.56** |
| Cryosupernatant | 292 | .17 | 49,640 | 168 (loss) | — | — | — | — |
| Cold Tris extract (impurities) | 10.9 | .29 | 3,161 | 11 (loss) | 4.3 | .5 | 0.067 | 4 |
| AHF extract | 9.57 | 12.2 | 116,730 | 396 | 21.6 | 16.8 | 0.565 | 35 |
| Final AHF concentrate Before lyophilization | 8.47 | 9.5 | 80,465 | 273 | 14.4 | — | 0.66 | 41 |
| After lyophilization | 3.39* | 24.2 | 82,000 | 278 | 36.0 | 22.3 | 0.672 | 42 |

*Calculated volume based on 25 ml fill and 10 ml reconstituted volume.
**Based on the assumed value of one Factor VIII unit and 62 mg protein/ml.

The product was filled in 25 ml aliquots in 50 ml bottles, quick-frozen in liquid nitrogen (freezing time 8–10 min.). and stored at −70° C prior to lyophilization. For assay and use, the lyophilized material was redissolved with 10 ml of water.

A quantitation of yields and recoveries of AHF concentrates by the present invention is shown in Table II.

A comparison of AHF concentrates prepared by the method of U.S. Pat. No. 3,652,530 and by the present invention is shown in Table III.

Table III

Comparison of AHF Concentrates Prepared by the Old and New Method

| | Old Method (U.S. Pat. No. 3,652,530) | New Method (present invention) |
|---|---|---|
| Potency per vial, Factor VIII units | 250 | 250 |
| Reconstituting volume, ml. | 25 | 10 |
| Vial size, ml. | 100 | 50 |
| Purification over plasma | 20–25 | 40–50 |
| Solubilizing time, minutes | <5 | <5 |
| Appearance | opalescent yellowish | clear trace yellowish |
| Overall Factor VIII recovery per liter plasma | ~250 | ~250 |

It is thought that the invention and many of its attendant advantages will be understood from the foregoing description, and it will be apparent that various changes may be made in the method as described herein without departing from the spirit and scope of the invention or sacrificing its material advantages, the forms hereinbefore described being merely preferred embodiments thereof.

It is claimed:

1. In a method for the preparation of purified AHF which includes the thawing of frozen plasma at a temperature of between about 0° and about 1° C to obtain a cryoprecipitate containing AHF, the improvement which comprises:

(a) extracting said cryoprecipitate with a low ionic strength buffer solution comprising tris (hydroxymethyl) aminomethane at a temperature of about 0° C to obtain a cold insoluble fraction having cold soluble impurities removed therefrom;

(b) extracting said cold insoluble fraction with a low ionic strength buffer solution comprising tris (hydroxymethyl) aminomethane at a temperature of about 21° C to obtain a solution comprising AHF and said buffer solution;

(c) deprothrombinizing said solution with aluminum hydroxide gel; and (d) recovering an AHF-rich solution.

2. The method of claim 1 wherein, in steps (a) and (b), a buffer solution having a concentration of about 0.005 to about 0.04 M is employed at a pH of 7.00.

3. The method of claim 1 wherein, in step (a), about 4 ml of a 0.02 M buffer solution are employed per gram of the cryoprecipitate.

4. The method of claim 1 wherein in step (b), about 2 ml of a 0.02 M buffer solution are employed per gram of the cryoprecipitate.

* * * * *